United States Patent [19]

Dietz

[11] Patent Number: 5,005,571

[45] Date of Patent: Apr. 9, 1991

[54] MOUTH NOSE MASK FOR USE WITH AN INHALATION THERAPY AND/OR BREATHING MONITORING APPARATUS

[76] Inventor: Henry G. Dietz, 80 Salisbury Ave., Garden City, N.Y. 11530

[21] Appl. No.: 276,293

[22] Filed: Nov. 25, 1988

[51] Int. Cl.[5] .............................................. A62B 18/02
[52] U.S. Cl. .......................... 128/205.25; 128/206.11; 128/207.18
[58] Field of Search ...................... 128/204.18, 204.21, 128/204.23, 204.26, 205.11, 205.25, 206.11, 206.12, 206.24, 206.28, 207.18

[56] References Cited

U.S. PATENT DOCUMENTS

| | | | |
|---|---|---|---|
| 1,362,766 | 12/1920 | McGargill | 128/206.11 |
| 1,873,160 | 8/1932 | Sturtevant | 128/206.11 |
| 2,178,800 | 11/1939 | Lombard | 128/205.11 |
| 2,831,487 | 4/1958 | Tafilaw | 128/207.18 |
| 4,201,205 | 5/1980 | Bartholomew | 128/205.25 |
| 4,207,888 | 6/1980 | Ghormley | 128/206.24 |
| 4,231,363 | 11/1980 | Grimes | 128/205.25 |
| 4,263,908 | 4/1981 | Mizerak | 128/207.18 |
| 4,454,880 | 6/1984 | Muto et al. | 128/207.18 |
| 4,457,303 | 7/1984 | Durkan | 128/204.26 |
| 4,685,456 | 8/1987 | Smart | 128/207.18 |

Primary Examiner—Edgar S. Burr
Assistant Examiner—Aaron J. Lewis

[57] ABSTRACT

A mouth nose mask used in combination with an inhalation therapy and/or breathing monitoring apparatus, the mask is mounted on the face of a patient independently of a nasal cannula and over the cannula without impeding its function. The mask makes it possible for the cannula to carry out a dual function of providing inhalation therapy and breathing monitoring both through the nasal passages of the patient and oral cavity of the patient. The mask has no connections to the inhalation therapy and breathing monitoring apparatus and is worn over the nasal cannula. In use, the treatment gaseous fluid is delivered to a patient through the nasal passages in communication with the nasal cannula. The mask provides for diversion of some of the oral inhalation air to the nasal cannula to sense inhalation in the event that the upper nasal passages of the patient are blocked. Moreover, the mask will effect diversion of some of the treatment gaseous fluids to the oral cavity when the patient's upper nasal passages are blocked.

2 Claims, 6 Drawing Sheets

MOUTH NOSE MASK FOR USE WITH AN INHALATION THERAPY AND/OR BREATHING MONITORING APPARATUS

BACKGROUND OF THE INVENTION

This invention relates generally to mouth nose masks, and more particularly to one that does not hinder normal breathing and allows a nasal cannula to be used for a single function or for dual functions of sensing inhalation and delivering a fluid, such as oxygen, when a human breathes either through the nose or mouth.

Nasal cannulas are commonly employed in the administration of gaseous fluids, such as oxygen, into the nasal passages of a convalescent human or those having respiratory ailments. Illustrations of nasal cannula can be found in U.S. Pat. No. 3,802,431. Nasal cannulas have been in use for a relatively long time for inhalation therapy.

The use of a nasal cannula for sensing inhalation has been recently accomplished and made possible by the development of highly sensitive inhalation sensors such as described in U.S. Pat. No. 4,745,925. A nasal cannula can be used for monitoring breathing and detecting apnea (the absence of breathing) by being connected to a highly sensitive inhalation sensor. The dual functions of sensing inhalation and administering fluids, such as oxygen, can be accomplished with a single cannula to determine the on-set of inspiration to trigger delivery of a specific dose of a respiratory gas through the same nasal cannula that is sensing inhalation.

A nasal cannula has the disadvantage that when a human breathes through his mouth the nasal cannula can not sense inhalation. A blockage of the upper nasal passageways, causing mouth breathing, can prevent proper administering of fluids, such as oxygen, to a human.

The purpose of the mouth nose mask which is positioned adjacent to a human's face and worn over a nasal cannula, is to deliver fluid being administered by a nasal cannula to a human's nose, or to the oral cavity when a human breathes through his mouth. Likewise, when a nasal cannula is used for sensing inhalation, a blockage of the mask user's upper nasal passages will result in some of the oral inhalation being diverted to a nasal cannula to allow sensing inhalation.

The advantage of using a nasal cannula for sensing is that a nasal cannula is more efficient, in that the most difficult sensing of inhalation is when breathing occurs through the nose, since the negative pressure can be as little as 0.001 of an ounce per square inch. A nasal cannula is most efficient in connecting the human nasal passageways to a highly sensitive inhalation sensor to detect the low negative inhalation pressure at a human's nostrils.

If a nasal cannula is replaced by a more common mouth nose mask used for inhalation therapy, with a connection to a sensor, it would be necessary for such a mask to have an air-tight fit to a human's face since the slightest leak will cause loss of the very low nasal negative pressure of inhalation. Such a mask, with connection to a sensor, would also require a valve that would close when a human inhales, and it would not be possible to mix outside air with fluids, such as oxygen, being administered.

The present mouth nose mask need not be an air-tight fit, as it has no valve and has an opening to the outside air, it is only required to divert a small amount of the large inhalation pressure from the oral cavity to a nasal cannula for sensing and allows air to enter the mask for mixing with a gas being administered. The construction of the mouth nose mask, according to the invention, is so simple, that it can be made disposable for single human use.

SUMMARY OF THE INVENTION

The present invention provides a mouth nose mask having a formed seal of a soft flexible material, such as clear flexible polyvinyl chloride, that is suitable for vacuum forming or injection molding, to produce a seal that is supported by the user's chin and upper section of the nasal bone. The seal adapts to the contours of a user's face. A second sheet consisting of a flat more rigid material, such as a rigid sheet polyvinyl chloride, that is suitable for die cutting and vacuum forming or injection molding, is provided to produce a plate for fastening the flexible seal onto. The flat rigid plate for fastening also includes an opening, a formed projection for clearance of the user's nose, and means for attaching two adjustable elastic straps for securing the mouth nose mask to the user's face. The mouth nose mask is worn over the nasal cannula and has no connections to any external fluid supply system.

The invention provides for the administration of fluid being delivered to the nose of a human by means of a nasal cannula and the use of a nasal cannula as a means of detecting inhalation to detect apnea (the absence of breathing).

If a nasal cannula is used without the mouth nose mask, the nasal cannula has the disadvantage that if the wearer breathes through the mouth, a nasal cannula will not function. The advantage of using a nasal cannula for sensing is that a nasal cannula is more efficient in detecting nasal inhalation when breathing occurs through a nose. Inhalation negative pressure at a human's nostrils can be as little as 0.001 of an ounce per square inch. A nasal cannula is most efficient in connecting the human nasal passageways to a highly sensitive inhalation sensor, such as in U.S. Pat. No. 4,745,925, to detect the low negative inhalation pressure at a human's nostrils.

The mouth nose mask makes it possible for the nasal cannula to function when the mask user's upper nasal passageways are blocked and breathing takes place through the mouth.

The mouth nose mask need not be an air-tight fit, as it has no valve and has an opening to the outside air. Its purpose is to divert a small amount of the large inhalation pressure from the oral cavity to a nasal cannula when the user's upper nasal air passageways are blocked and breathing takes place through the mouth.

The mouth nose mask also allows fluids being delivered by a nasal cannula to enter the mask and be inhaled orally when upper nasal passageways are blocked and breathing takes place through the mouth.

A principal object of the invention is that it enables a nasal cannula to function when breathing takes place through either the mouth or nose.

Another principal object of the mouth nose mask is that it makes it possible for an ordinary nasal cannula used in hospitals for administering oxygen to a human, to be used for connecting a human's nasal airflow to an inhalation sensor which will continue to function sensing inhalation when the user's upper nasal passageways are blocked and breathing takes place through the mouth.

Another principal object of this invention of the mouth nose mask is that when a cannula is used for delivering a fluid to a patient's nasal passageways a blockage of the upper nasal passageways will result in fluid being delivered by a cannula to enter the mask where it can be mixed with outside air and be inhaled into the patient's oral cavity.

Still another object of the invention is its simplicity of construction and can be made disposable for a single use.

Another object of the invention is that it need not be an air-tight fit or require a valve to function.

The mouth nose mask can be used with a nasal cannula to trigger a prescribed dose of therapeutic gas when inhalation takes place either through the nose or the mouth.

The mouth nose mask is also used to detect apnea (the absence of breathing) when inhalation takes place either through a nose or mouth.

In industrial applications it is possible to supply a controlled high rate of respiratory gas for breathing when inhalation takes place, so that the mask is always at a positive pressure to flush out contaminants from being breathed in from outside environments when inhalation is taking place.

The mouth nose mask makes possible the use of equipment designed only for intermittent flow delivery of fluids by a nasal cannula and to also function when breathing is accomplished through the user's mouth, such as when sleeping.

BRIEF DESCRIPTION OF THE DRAWINGS

Other features and objects of the mouth nose mask will be understood from the claims and appended drawings in which:

DESCRIPTION OF PREFERRED EMBODIMENTS

Figure 1:
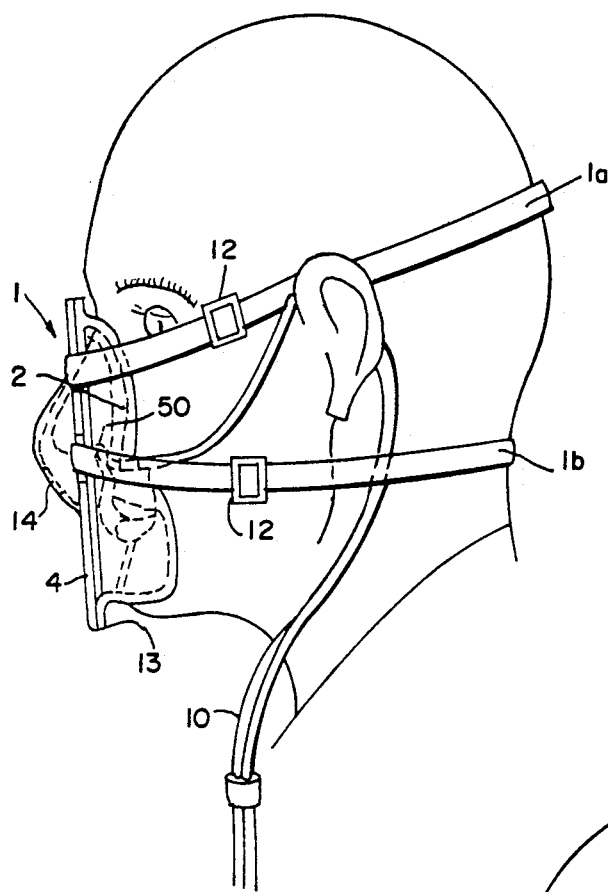
FIG. 1 is a side elevation view of the mouth nose mask, worn over a nasal cannula, according to the invention.

The foregoing and other objects, features, and advantages of the invention are more apparent from the following particular description of preferred embodiments, as illustrated in the accompanying drawings in which reference characters refer to the same parts throughout the various views. The drawings are not to scale, emphasis instead being placed upon illustrating the invention.

Figure 2:
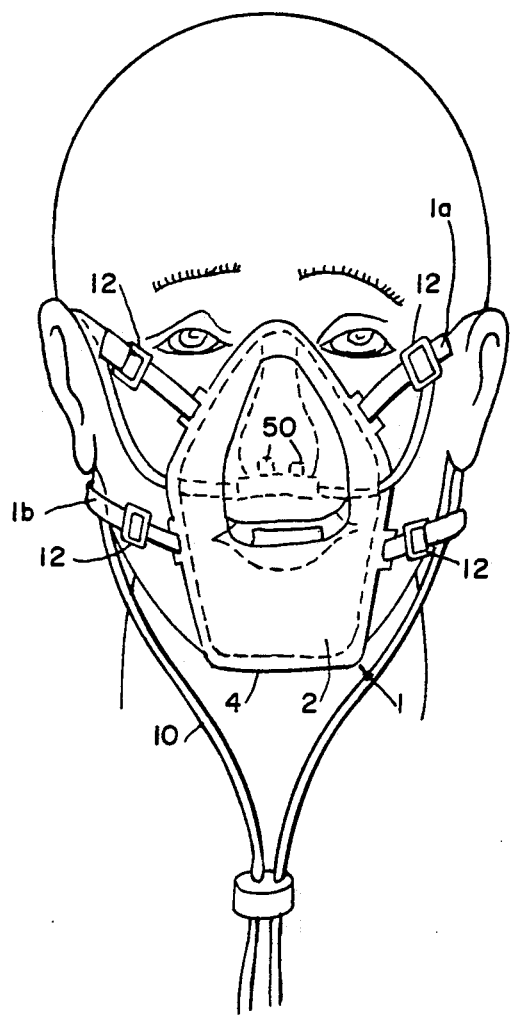
FIG. 2 is a front elevation view of the mouth nose mask worn over a nasal cannula according to the invention.
Figure 3:
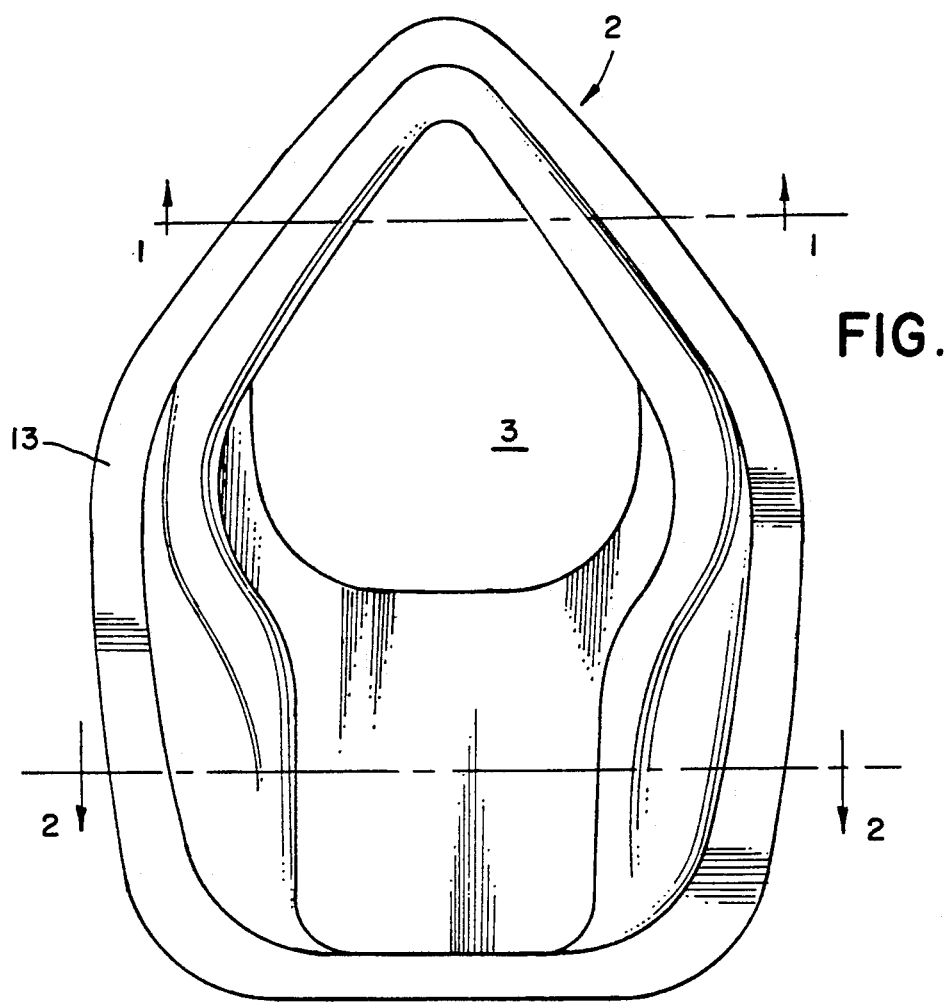
FIG. 3 is a plan view of a formed seal that is supported by the chin and upper section of the nasal bone and adapted to the contours of a user's face, according to the invention.
Figure 6:
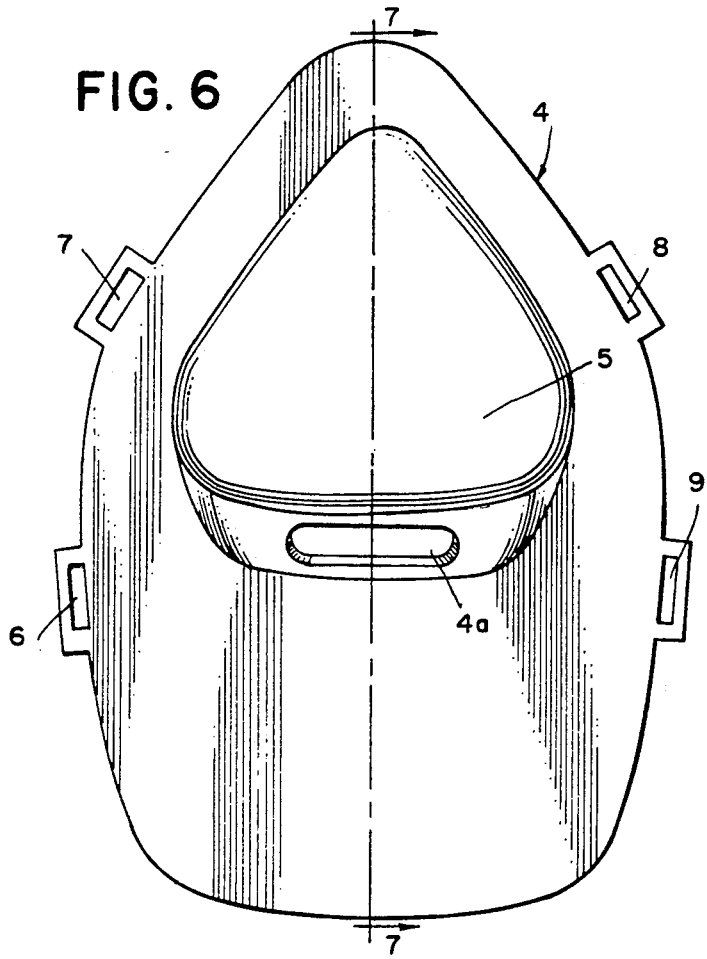
FIG. 6 is a plan view of a plate for fastening the flexible seal of FIG. 3 onto, in accordance with the invention.
Figure 8:
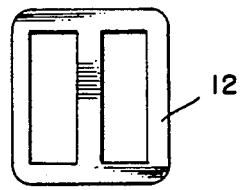
FIG. 8 is a plan view of a buckle used for making attachment straps adjustable.
Figure 9:
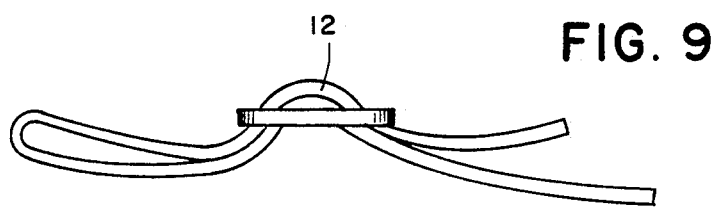
FIG. 9 is a top view of the buckle shown in FIG. 8 with its corresponding use to make attachment straps adjustable in accordance with the invention.

FIGS. 1 and 2 generally illustrate a preferred embodiment of the mouth nose mask as worn by a human, comprising the formed seal 2 illustrated in FIG. 3, attached to a plate 4 illustrated in FIG. 6, by a suitable bonding agent. The assembled mouth nose mask is adapted for mounting on a human face by being supported by the chin and the bridge of the nose or the upper nasal bone while adapting to the contours of a user's face and is held in place by two elastic straps 1a and 1b that are fastened to a plate illustrated in FIG. 6 by means of buckles 12, illustrated in FIG. 8. FIG. 9 illustrates how elastic straps are threaded through the buckles 12 to provide means for fastening and adjusting elastic straps to the mouth nose mask.

Figure 4:
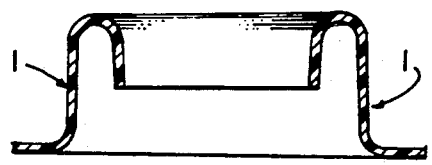
FIG. 4 is a section view taken along section line 1—1 of FIG. 3.

The formed seal 2 illustrated in FIG. 3 is manufactured using a soft and flexible material, such as a biodegradable papier-mache or a clear flexible polyvinyl chloride, that is suitable for vacuum forming or injection molding to produce the formed seal. The seal 2 is supported by the chin and upper section of the nasal bone, while adapting to the contours of the face of a user wearing the mask. FIG. 4 is a section view taken along section line 1—1 of the formed seal 2 in FIG. 3 and illustrates how seal 2 is shaped to fit the contours of the upper nasal bone or bridge of a human's nose.

Figure 5:
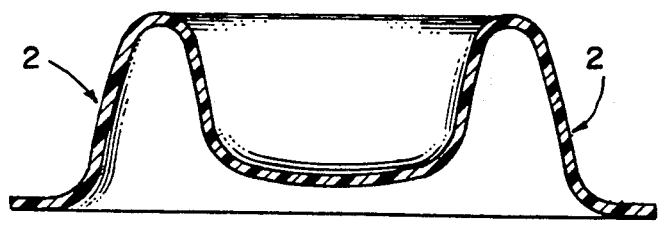
FIG. 5 is a section view taken along section line 2—2 of FIG. 3.

FIG. 5 is a section view taken along section line 2—2 of the formed seal 2 and illustrates how the seal 2 is shaped to fit the contours of the chin of a human. An opening 3 is provided in the formed seal 2 so that a fluid, such as oxygen, may enter either the nose or mouth when the mouth nose mask FIG. 1 is worn by a human user. The flange 13 of FIG. 3 is to provide a flat surface to aid in attaching the formed seal FIG. 3 to the plate FIG. 6.

Figure 7:
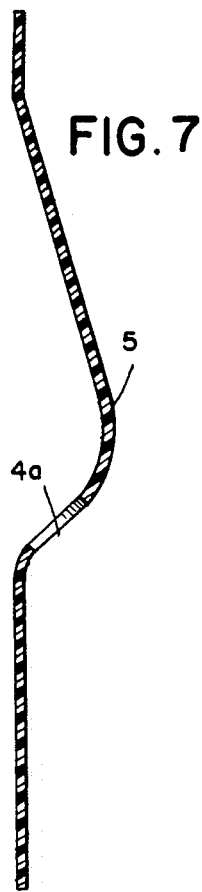
FIG. 7 is a section view taken along section line 7—7 of FIG. 6.

A plate 4, illustrated in FIG. 6, manufactured using a flat sheet of more rigid material than the material used in the formed seal 2, such as a biodegradable papier-mache or a rigid sheet of polyvinyl chloride that is suitable for die cutting and vacuum forming or injection molding, is attached to the formed seal 2 by a suitable bonding agent. The plate 4 has an opening 4a that is used to provide an opening to the exterior of the mask. A formed projection 5 is provided for clearance of the nose of the user, and four rectangular openings 6, 7, 8, and 9 for attaching the two adjustable straps 1a and 1b for securing the mouth nose mask to the face of the user. FIG. 7 is a section view taken along lines 7—7 of the plate illustrated in FIG. 6 and shows cutout 4a and formed projection 5 for clearance of the user's nose. The mouth nose mask, FIGS. 1 and 2, is worn over a nasal cannula 10 that is connected to inhalation sensor 11. The mouth nose mask has no connections to any external fluid supply system, and a human wearing the mouth nose mask depends upon a nasal cannula for the fluid supply obtained from the inhalation therapy apparatus described in this patent.

A nasal cannula 10 is also used for sensing when inhalation takes place. The advantage of using a nasal cannula 10 for sensing is that the nasal cannula 10 is more efficient in that the most difficult sensing of inhalation is when breathing occurs through the nose, for the negative pressure can be as little as 0.001 of an ounce per square inch. A nasal cannula 10 is most efficient in connecting human nasal passageways to the highly sensitive inhalation sensor 11 to detect the low negative inhalation pressure at a human's nostrils. A disadvantage of using a nasal cannula 10 is when a human breathes through his mouth the nasal cannula 10 can not sense inhalation and an existing blockage of upper nasal passageways, causing mouth breathing, can prevent proper administering of fluids, such as oxygen, to the human user. The mouth nose mask according to the present invention eliminates the above disadvantage by making it possible to allow the nasal cannula 10 to function when the human user breathes either through the nose or mouth, without hindering breathing.

The mouth nose mask need not be an air tight fit or have any valves; it has openings 3 and 4a to the exterior of the mask. The purpose of the mask is to divert a small amount of the large inhalation pressure from the oral cavity of the user to the nasal cannula 10 when the user's upper air passageways are blocked and breathing takes place through the mouth. The negative pressure created by the oral cavity when the upper nasal passageways are blocked is measured in approximately tenths of an inch of water column pressure when inhalation takes place and is greater in volume than the volume of air inhaled by the nose. If the patient is breathing through his mouth and the upper nasal passageways are blocked, the oral negative pressure will reduce the pressure within the mouth nose mask. The nasal cannula has tubular openings 50 extending into the lower nasal passageways of the nose, but these tubular openings 50 are much smaller than the lower nasal passageways. There is considerable clearance between the lower nasal passages and the tubular openings 50 of the cannula so that the negative inhalation pressure of the mouth nose mask reduces the pressure in the lower nasal passageway when the upper nasal air passageways are blocked, which results in the tubular openings 50 of the cannula receiving a negative pressure. Since the inhalation sensor connected to the nasal cannula can actuate at pressures such as 0.002 inches of water column, the oral negative pressure such as 0.2 of an inch of water column when reduced by the openings 3 and 4a of the mouth nose mask and by leakage created by loose fitting of the mouth nose mask unit will retain a remaining negative pressure that will be sufficient to actuate the inhalation sensor connected to the nasal cannula since the sensor will detect values as low as 0.002 of an inch of water column negative pressure.

The mouth nose mask allows fluids being delivered by the nasal cannula 10 to enter the mask, and be inhaled orally when the upper nasal passageways are blocked and breathing takes place through the mouth. Fluids are delivered to the nasal cannula when inhalation takes place. If the upper nasal passageways are blocked, the fluid is not sucked into the nose but escapes from the tubular openings 50 into the lower nasal passageway for there is considerable clearance between the lower nasal passageway and tubular openings 50 of the cannula. Oral inhalation creates a negative pressure in the mouth nose mask and the fluid in the lower nasal passageway is sucked into the mouth nose mask. The fluid in the mouth nose mask is sucked into the oral cavity that is at a higher negative pressure than the negative pressure in the mouth nose mask when oral inhalation takes place.

The mouth nose mask, is intended to be used with inhalation therapy and monitoring devices. One of the preferred embodiments for inhalation therapy is described, but it will be understood by those skilled in the art that various other types of apparatus, such as for monitoring breathing, can be used with the mask.

Figure 10:
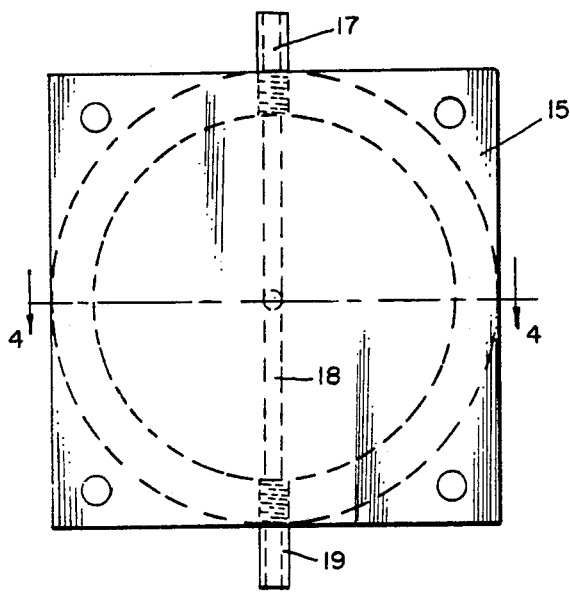
FIG. 10 is a top view of an optoelectronic sensor according to the invention.
Figure 11:
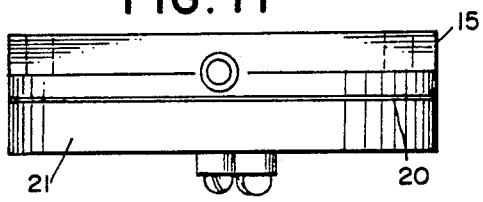
FIG. 11 is a front elevation view of an optoelectronic inhalation sensor according to the invention.
Figure 13:
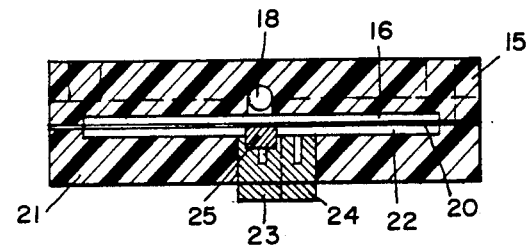
FIG. 13 is a section view taken along section line 4—4 of FIG. 10.
Figure 12:
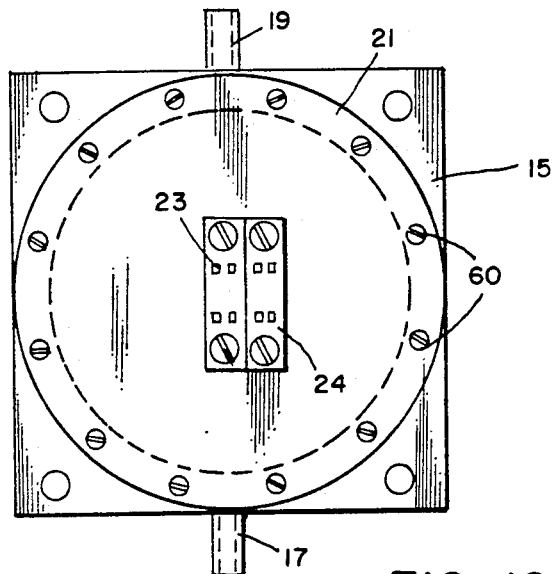
FIG. 12 is a bottom view of an optoelectronic inhalation sensor, according to the invention.
Figure 14:
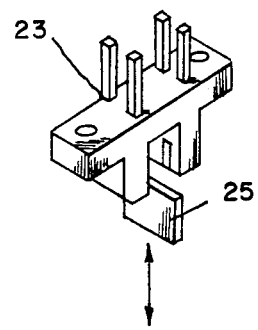
FIG. 14 is a diagrammatic view of an optoelectronic solid state photo coupled interrupter module according to the invention, used in an optoelectronic inhalation sensor, and shown in isometric projection.

FIGS. 10, 11, and 12 generally illustrate a preferred embodiment of an optoelectronic inhalation sensor, which comprises a square housing 15, made of a rectangular opaque electrical non-conductor illustrated in cross section FIG. 13, having a circular recess forming a central cavity 16 therein. The square housing 15 has an inlet connection 17, through one end thereof, communicating with a passageway 18, and another outlet connection 19, through 19 the other end of the square housing 15. Both inlet and outlet passages are in direct communication with the central cavity 16 in the square housing 15.

With the flow of inhalation therapy gas into the inlet connection 17, passageway 18 communicating with outlet connection 19, creates a suction in the central cavity 16. This slight suction is used to clear out any moisture that may have been entrapped in the central cavity 16, which, if not removed, could affect operation of the sensor. A diaphragm 20 made as a 0.0005 inch thick polyester film or other equally suitable thin flexible material, is provided in the housing as shown. The diaphragm 20 is pre-stressed circumferentially and is bonded to a surface of the square housing 15 and forms a space between the recessed central cavity 16 of the housing 15 and the film flexible diaphragm 20. This space changes in volume when a patient inhales, becoming smaller when inhalation takes place and the diaphragm flexes. A clamping disc 21, made of opaque electrical non-conductor material, FIG. 13, having a circular recess forming a central cavity 22, is fastened to the square housing 15 by a plurality of screws 60. The circular recess defining the lower central cavity 22, is vented to the outside atmospheric pressure. The depth of the circular recess forming the central cavity 22 is minimum, such as 0.0005 inch deep, and is used to limit the flexing movement of the film diaphragm 20 to prevent the film diaphragm 20 from being stretched when inhalation therapeutic gases with a high pressure of ten pounds per square inch are supplied to the upper central cavity 16. For best operation of the optoelectronic inhalation sensor, the clamping disc 21 is located at the bottom of the sensor. With changes in temperature, the diaphragm 20 can expand or contract. However, due to the limited depth of the recess, and due to the force of gravity the diaphragm 20 will always be in close proximity to the set calibration point, which is the point where the film diaphragm 20 is flat with no pressure on either side thereof.

In the center of the clamping disc 21 is disposed a rectangular opening to accept two optoelectronic solid state photon coupled interrupter modules 23 and 24. The module 23 is located in the center of the disc 21 and provides an electrical output when the infrared-opaque vane 25 is moved upwardly by the film diaphragm 20. The vane 25 is fastened to the center of the film diaphragm 20. The module 24 is located as near as possible to the module 23. The module 24 is used as an inactive unit to provide a reference for temperature compensation.

The electrical output of the optoelectronic solid state photon coupled interrupter module 23 occurs when a negative inhalation pressure is applied to the upper central cavity 16 moving the vane 25 upwardly to allow passage of the infrared light. This puts the other module 23 in the same design category as a mechanical precision limit switch, except that the activating vane 25 is blocking light instead of applying force. Thus, mechanical wear and deformation effects are eliminated. If mechanical precision limit switches were used it would be necessary to make them mechanically adjustable so that the actuating point of the switches would occur when the diaphragm 20 was displaced a critical distance. Using the optoelectronic module 23 makes it possible to adjust the actuating point electrically since adjusting the sensitivity of the detector is equivalent to moving a mechanical precision limit switch in and out from the diaphragm 20.

The diaphragm 20 will be activated by a small volume of negative inhalation pressure of 0.001 ounce per square inch, which will move the infrared-opaque vane 25 up to signal switching the output from an "Off" state to an "On" state. The "On" state will trigger a prescribed dose of therapeutic gas at high pressure forcing the diaphragm 20 into the lower central cavity 22, and preparing it for the next inhalation, when the diaphragm 20 will be sucked up into the upper central cavity 16.

Figure 15:
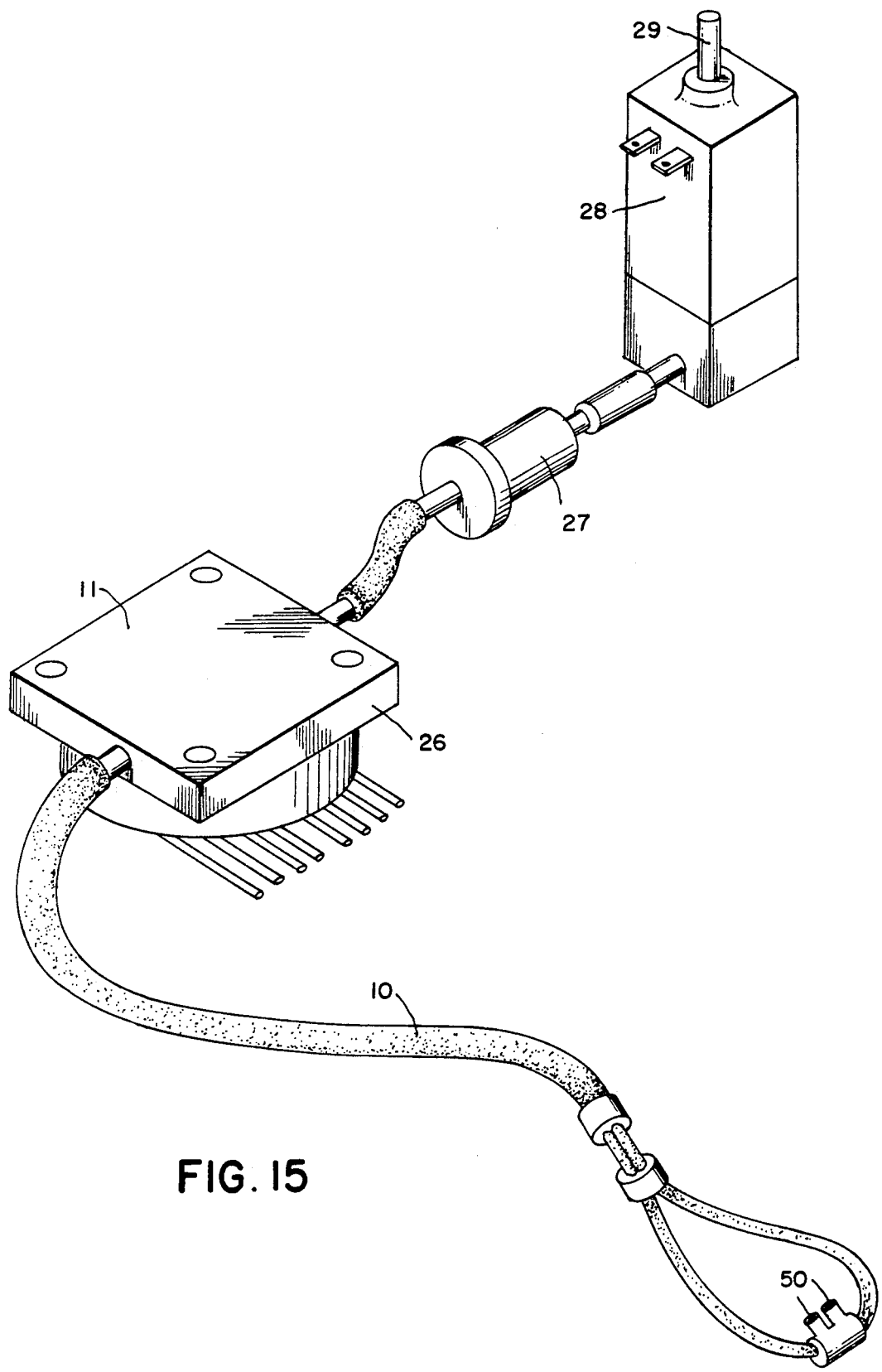
FIG. 15 is a diagrammatic view using an optoelectronic inhalation sensor for inhalation therapy and illustrated in isometric projection.

FIG. 15 illustrates one method and an apparatus for using an optoelectronic inhalation sensor for inhalation therapy. A cannula 10 commonly available in hospitals for administering oxygen, is used to connect the flow of air from a patient's nostrils to the optoelectronic inhalation sensor 26 described above, by using the outlet connection 19, FIG. 10. A filter 27 can be placed as shown on FIG. 15 or inserted between the cannula 10 and optoelectronic inhalation sensor 26. Its purpose is to prevent any foreign object, that might be present in the gas supply, being inhaled into the patient's lungs.

The optoelectronic inhalation sensor 26 is connected to a normally open solenoid valve 28 by means of appropriate tubing using the inlet connection 17 of the inhalation sensor 26. The solenoid valve 28 is electrically actuated by a low voltage and a low current, that can be supplied by an electronic circuit that can be designed in known manner to be intrinsically safe (a circuit that is incapable of having a spark or thermal effect that would be capable of causing ignition of flammable or combustible material in the gas being used for inhalation therapy). A connection 29 on the solenoid valve 28 is connected to the supply of gas being used for therapy. In hospitals, a flow meter and pressure regulator are usually available at the patient's bedside and supply a constant flow of gas (such as 0 to 10 liters of oxygen per minute). Present day practice is for hospitals to have oxygen piped permanently into each room used for patient's care. For home use where oxygen is delivered in tanks, the apparatus supplied with such tanks includes some type of flow meter and a pressure regulator. The cannula 10 is adjusted to fit the patient so that the two prongs 50 are inserted into the patient's nostrils. The inhalation flow of air from the patient's nostrils produces a very low pressure or vacuum at the end connected to the inhalation sensor 26.

The vacuum pressure produced by the patient inhaling is no more than a few thousandths of an ounce per square inch. At the time the patient is exhaling, the electric solenoid valve 28 is electrically activated and shuts off the flow of gas from the therapeutic gas being used. When the patient inhales, the thin film diaphragm 20 is sucked up and flexes into the upper central cavity 16, moving the infrared-opaque vane 25 upward to cause an electrical signal to an "On" state. With appropriate electrical circuits as described herein, a signal is sent for a pre-determined time to cause a flow of therapeutic gas by electrically deactuating the normally open valve 28. In actual practice, it has been found that the flow of air being sucked in by the patient is at a maximum for only a very short period of time, and this peak flow of air vacuum from the patient's nostrils is used to trigger the flow of the therapeutic gas for a pre-set time.

The length of the pre-set time can be adjusted for the correct flow of therapeutic gas for the normal adult rate of fourteen to twenty breaths per minute, or for twenty to forty breaths for babies and toddlers. The respiration rate rises as much as four breaths per minute for every degree of patient's temperature over normal.

The pre-determined time therefore, provides for an intermittent flow of therapeutic gas to the patient. The patient normally inhales approximately for 30% of the time for each breath, with 70% of the breath for exhaling. By setting the pre-set timer to 30% of the breath time, a savings of 70% of the therapeutic gas can be achieved over the normal hospital system of having a constant flow. It is also possible to apply the therapeutic gas at a very early stage of inspiration with a large volume of gas which will reach the alveoli and not waste additional gas that remains in the "dead spaces" such as the pharynx, trachea, and bronchial tubes.

At the time the therapeutic gas flows into the inhalation sensor 26, high pressure is applied to the diaphragm 20, causing it to be in close contact with the circular recessed surface of the central cavity 22, moving the infrared-opaque vane 25 downwardly to block the infrared light of the interrupter module 23. Therefore, upon completion of the pre-set time, a signal is sent by the inhalation sensor 26, to an electrical circuit that actuates the solenoid valve 28 to its closed position and shuts off the flow of therapeutic gas to the inhalation sensor 26, and the cannula 10. Upon completion of the patient's exhaling, the cycle of events will be repeated by the patient again inhaling.

Figure 16:
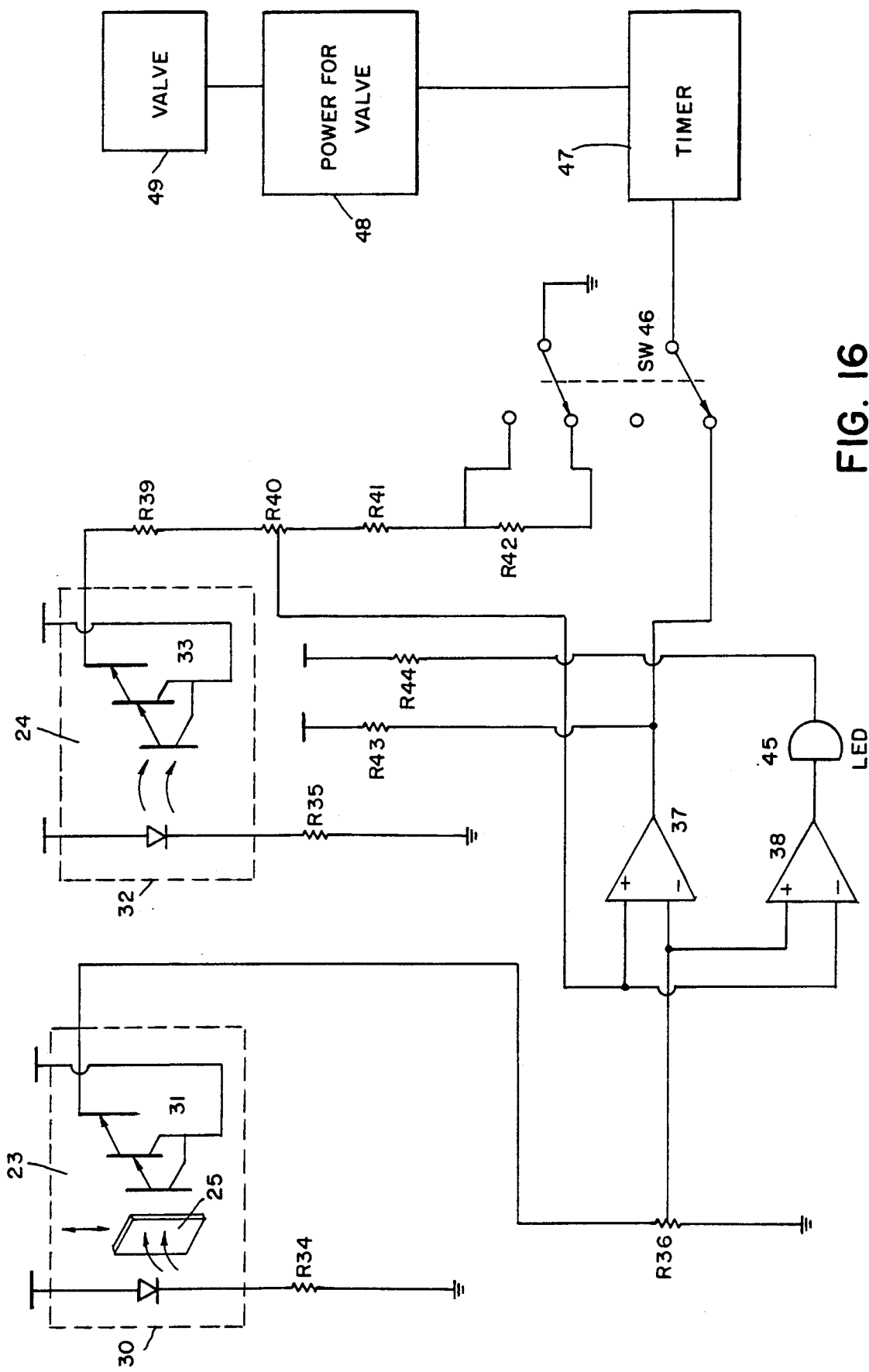
FIG. 16 is a schematic diagram and block diagram for using the inhalation sensor for inhalation therapy.

FIG. 16 illustrates a schematic diagram and block diagram of one of the preferred electrical circuits used to obtain intermittent flow of the therapeutic gas. Two optoelectronic solid state photon coupled interrupter modules 23 and 24 shown in FIG. 16 are the same modules 23 and 24 shown in FIG. 12 located in the inhalation sensor 26.

The module 23 is an interrupter module consisting of a gallium arsenide infrared emitting diode 30 coupled to a silicon darlington connected phototransistor 31, interrupted by the infrared-opaque vane 25. Vane 25 is actuated by the diaphragm 20 of the inhalation sensor 26. The module 24 is an interrupter module consisting of a gallium arsenide infrared emitting diode 32 coupled to a silicon darlington connected phototransistor 33, used as a temperature compensater to balance the temperature changes of module 23. Resistors 34 and 35 are current limiting resistors connected for keeping the power dissipation below maximum ratings of the infrared emitting diodes 30 and 32.

The output of the darlington connected phototransistor 31 is fed into a loading resistor R36, which is a potentiometer allowing for a variable adjustable voltage tap to feed into an inverting input of two voltage comparators 37 and 38. In like manner, the output of the darlington phototransistor 33 is fed into the series loading resistors R39, R40, R41 and R42. The resistor R40 allows for a variable adjustable voltage tap to feed into the non-inverting input of the voltage comparators 37 and 38.

An output voltage of the comparators 37 and 38 will swing from full on to full off when the voltages applied to the inputs differ by only about 0.001 volt. Thus a very small movement of the vane 25 will produce a very small voltage change that will result in the output of the comparators 37 and 38 swinging from full off to full on with the voltage being applied to the output resistors R43 and R44. An LED 45 will be illuminated each time the patient exhales, and is extinguished each time the patient inhales. A switch SW46 is used for calibrating the sensor. The switch, as shown in FIG. 16 is positioned for normal operation after calibration has taken place.

Placing the switch SW46 in the calibration position results in the series resistor R42 not being in the output load of the darlington connected phototransistor 33, and in disconnecting the output of the voltage comparator 37. With the switch in the calibration position, the potentiometer R40 is adjusted (with the cannula 10 disconnected) so that the LED 48 is made to just illuminate. This is the position of the potentiometer R40 where the position of the vane 25 will be most sensitive to the movement of the diaphragm 20 when inhalation occurs.

The potentiometer R36 is adjusted so that the LED 45 will be just illuminated when potentiometer R40 is set at the mid point. When the sensor is adjusted for maximum sensitivity, the slightest change in the calibration point will cause undesired oscillation because the high pressure of the triggered dose of therapeutic gas is inadvertently being fed back into the input of the sensor causing parasitic oscillations which could mimic the breathing of the patient.

The invention deals with this difficulty by providing mechanical and electrical means to offset and prevent significant changes in the calibration point of the diaphragm. The diaphragm 20 is affected by gravity and temperature. An increase in temperature will cause the diaphragm 20 to expand and gravity will act to pull the diaphragm downwardly. This difficulty is overcome by limiting the distance (to a very small distance, such as 0.005 inch) that the diaphragm can move to the central cavity 22 of the clamping disc 21.

When the high pressure of the triggered dose of therapeutic gas is applied to the diaphragm 20, the diaphragm 20 is prevented from being stretched beyond its limit of elasticity and beyond the point where the material will expand and return to its original shape only after a time delay. A diaphragm that would be allowed to expand to a point where it would be necessary for it to remember its original shape, with a time delay, would cause a shifting of the calibration point and undesirable parasitic oscillations. Temperature changes and aging of the interrupter module 23 could also cause shifting of the calibration point and undesirable parasitic oscillations.

This is overcome in the mask according to the invention by using a second interrupter module 24 to obtain the reference voltage comparators 37 and 38. The temperature and aging characteristics of the interrupter 23 is compensated for by the identical temperature and aging characteristics of the interrupter 24. Since the calibration point is set at the maximum sensitivity, the slightest change in the balance of the circuit due to shift in the calibration point, would cause the unit to become inoperable. To prevent very small changes of the calibration point from affecting the operation of the sensor, the series resistor R42 is added to the output loading resistors R39, R40, and R41 to desensitize the circuit and make it less affected by very slight changes in the calibration point.

When the calibration switch SW46 is positioned as shown in FIG. 16, the output of the voltage comparator 37 is fed into a timing circuit 47. The timing circuit 47 is triggered by the patient's inhaling and results in an output that is for a pre-set time interval that provides power for a valve 49 to actuate the valve 28, giving the patient a dose of oxygen. The inhalation sensor 26 can be used to monitor breathing by using widely available known electrical circuits.

It is also possible to combine the functions of inhalation therapy and monitoring as shown in the inventor's pending application, "Method And Apparatus For Using An Inhalation Sensor For Monitoring And For Inhalation Therapy", Ser. No. 06/831,181, filed 2/20/86.

The inventor's U.S. Pat. No. 4,745,925 also provides for fail-safe operation; a continuous flow of oxygen will be provided in case of failure of the sensor 26 to operate.

While the invention has been particularly shown and described with references to the preferred embodiments thereof, it will be understood by those skilled in the art that various alterations in form and detail may be made therein without departing from the spirit and scope of the invention. Moreover, while the invention has been particularly shown and described for clinical use (as with a human patient for example), it should be understood the invention may be used in conjunction with gas supply or apnea detector in a subject in industrial, aeronautical, subterranean or underwater environments.

I claim:

1. A mouth nose mask which covers the mouth and nose in combination with a nasal cannula to function during breathing cycles of humans when breathing through the nose or mouth comprising:
    a formed seal of flexible material adapting to the contours of a human face and being supported by the chin and the upper nasal bone,
    means within said formed seal for allowing the passage of outside air into the mask,
    means bonded to said formed seal including a flat plate having an opening for the passage of outside air into the mask, a formed projection for nose clearance and means for supporting said mask on a human face including four holes within said plate and four straps,
    means connectable operatively through said mask to the respiratory system of a human for sensing inspiration.

2. A mouth nose mask as recited in claim 1, further comprising:
    means for supplying fluids being delivered at each inspiration during each breathing cycle of said animal or human during said breathing thereof.
    means for sensing individual negative pressures developed at each inspiration during each breathing cycle of said animal or human during said breathing thereof.

* * * * *